United States Patent [19]

Kimata et al.

[11] Patent Number: 5,302,633
[45] Date of Patent: Apr. 12, 1994

[54] OPTICAL RESOLUTION AGENT AND PROCESS FOR THE PREPARATION OF THE SAME

[75] Inventors: Kazuhiro Kimata; Riyo Tsuboi, both of Kyoto, Japan

[73] Assignee: Nacalai Tesque, Inc., Kyoto, Japan

[21] Appl. No.: 988,113

[22] PCT Filed: May 28, 1992

[86] PCT No.: PCT/JP92/00696

§ 371 Date: Jan. 26, 1993

§ 102(e) Date: Jan. 26, 1993

[51] Int. Cl.$^5$ ............................................. C08J 9/224
[52] U.S. Cl. .................................... 523/218; 521/54; 521/55; 521/57; 521/84.1; 521/109.1; 523/219
[58] Field of Search ................... 521/54, 55, 57, 84.1, 521/109.1; 523/218, 219

[56] References Cited

FOREIGN PATENT DOCUMENTS 142930A 7/1985 Japan.
196663A 10/1985 Japan.
226829A 11/1985 Japan.
226831A 11/1985 Japan.
226833A 11/1985 Japan.
160054A 7/1986 Japan.
162750A 7/1986 Japan.
162751A 7/1986 Japan.
211242A 8/1990 Japan.

Primary Examiner—Morton Foelak
Attorney, Agent, or Firm—Flynn, Thiel, Boutell & Tanis

[57] ABSTRACT

An optical resolution agent which is prepared by polymerizing a polysaccharide derivative having vinyl groups introduced into the hydroxyl groups thereof through an ester or urethane linkage on the surface of a porous support or by copolymerizing such a polysaccharide derivative having vinyl groups introduced thereinto with a porous support having vinyl groups introduced thereinto and which enables an efficient optical resolution of a racemic modification by chromatography.

6 Claims, 2 Drawing Sheets

OPTICAL RESOLUTION AGENT AND PROCESS FOR THE PREPARATION OF THE SAME

TECHNICAL FIELD

The present invention relates to an optical resolution agent and a process for the preparation of the same. Particularly, it relates to an optical resolution agent preferable as a packing for high-performance liquid chromatography which is prepared by polymerizing a vinyl derivative of a polysaccharide such as cellulose and the like on the surface of a porous support (particle) and a process for the preparation of the same.

BACKGROUND ART

It has been well known that a polysaccharide such as starch, dextran, cellulose, cellulose derivatives and the like exhibit respective unique optical resolving powers. Particularly, it has already been found that cellulose derivatives prepared by esterifying the hydroxyl groups of cellulose, i.e., chemically modified celluloses such as cellulose triacetate and the like are superior to cellulose itself in respect of optical resolving power.

When a substance as described above having an optical resolving power is as such used as a packing for liquid chromatography in the direct resolution of an optical isomer mixture by liquid chromatography, the service conditions of the column are disadvantageously narrowed, because the packing composed of the substance is poor in pressure resistance and is swollen or shrunken with the solvent used. In order to overcome this advantage, it is generally thought a means that the substance is supported on a support free from such problematic properties and the product is used.

Under these circumstances, the impregnation-adsorption process, i.e., a physical process which comprises dipping a support in a solution of the above substance, recovering the support and drying it occurs to us as one of the easiest processes for supporting the substance. However, the disadvantage still remains that only few kinds of solvents are usable when a measurement and an operation is conducted with a chromatograph, because it is undesirable to use a solvent which dissolves the substance. This disadvantage is generally more significant when a chemically modified polysaccharide is used. That is, the developer to be used in the chromatography using the modified polysaccharide must be one which does not dissolve the modified polysaccharide, because of the high solubility of the modified polysaccharide in an organic solvent, which restricts the selection of the resolution conditions severely. Further, there is also a limitation in the selection of the solvent to be used for dissolving a sample, because a chemically modified polysaccharide has a problem that the number of theoretical plates thereof is remarkably lowered even by the injection of only several microliters of a good solvent therefor.

Although the chemical bonding of a polysaccharide derivative as described above to a support may be thought to be effective in overcoming the above disadvantage of the physical process, no specific means have been proposed as yet on how to chemically bond the polysaccharide derivative to a support while maintaining the excellent optical resolving power of the polysaccharide derivative. For example, although Japanese Patent Publication-A No. 82858/1985 discloses that a chemical process as well as a physical one can be employed in supporting a polysaccharide derivative on a support, no specific description on the chemical process is found in this patent document.

DISCLOSURE OF THE PRESENT INVENTION

The present invention has been made under these circumstances and an object thereof is to provide a support for the optical resolution which uses a chemically modified polysaccharide (polysaccharide derivative) and which places little limitation on the developer to be used in liquid chromatography or the solvent to be used for dissolving a sample.

Namely, as the result of the extensively studies, the present inventors have found that a polymeric optically active support which is completely insoluble in a solvent exhibiting a high dissolving power for the chemically modified polysaccharide of the prior art, e.g., ethyl acetate, tetrahydrofuran, methylene chloride, chloroform, acetone, etc., can be obtained by, for the purpose of insolubilizing a chemically modified polysaccharide, chemically modifying the hydroxyl groups of a polysaccharide with a specified modifying agent having a vinyl group to form a polysaccharide derivative having vinyl groups introduced thereinto through an ester or urethane linkage and polymerizing the polysaccharide derivative on the surface of a porous support. The present invention has been accomplished on the basis of this finding.

Accordingly, the characteristic of the optical resolution agent of the present invention is that the agent is one prepared by polymerizing a polysaccharide derivative having vinyl groups introduced into the hydroxyl groups thereof through an ester or urethane linkage on the surface of a porous support, particularly advantageously one prepared by copolymerizing such a polysaccharide derivative with a porous support having vinyl groups introduced thereinto.

Further, the present invention also include that, for obtaining the optical resolution agent described above, a polysaccharide derivative having vinyl groups introduced into the hydroxyl groups thereof through an ester or urethane linkage is adhered or adsorbed on the surface of a porous support and then polymerization of the polysaccharide derivative is conducted, or that polymerization of such a polysaccharide derivative is conducted with at least part of the polysaccharide derivative being copolymerized with the vinyl groups of a porous support.

Although the polysaccharide into which vinyl groups are introduced according to the present invention is representatively cellulose, other polysaccharide such as dextran, amylose, curdlan, pullulan and the like may be suitably used. Further, it is desired that the cellulose to be used in the present invention have a low molecular weight corresponding to, for example, a number-average degree of polymerization of 100 or below for spreading a uniform cellulose derivative on a porous support uniformly, because the viscosity of a solution of a chemically modified cellulose prepared by the chemical modification of a cellulose increases as the molecular weight of the chemically modified cellulose increases, so that it becomes difficult more by more to cause the chemically modified cellulose to be adhered or adsorbed uniformly on the surface of a porous support.

The introduction of vinyl groups into such a polysaccharide by chemical modification must be conducted by introducing vinyl groups (specifically vinyl-containing organic groups) into the hydroxyl groups of a polysaccharide through an ester or urethane linkage in order to maintain the excellent optical resolving power of the polysaccharide.

The modifying agent to be used in the chemical modification of such a polysaccharide may be suitably selected from among known vinylic compounds which react with the hydroxyl group of a polysaccharide to form an ester or urethane linkage. Examples of the modifying agent include unsaturated acid halides such as acryloyl chloride, methacryloyl chloride, vinylbenzoyl chloride and the like; and unsaturated isocyanates such as vinylphenyl isocyanate and the like. Further, compounds having more than one vinyl group in the molecule as well as the above compounds having one vinyl group in the molecule may be used at need. Furthermore, in a case wherein a vinylic compound having a structure comprising a benzene ring and a vinyl group bonded to the ring is used, no significant trouble occurs with respect to the bonding position of the vinyl group even when the vinyl group is bonded to the ring at any of the ortho, meta and para positions, so far as the compound is polymerizable.

With respect to the introduction number of the vinyl group per a constituent unit of a polysaccharide when the chemically modification of a polysaccharide is conducted with a vinyl compound, all of the hydroxyl groups present in the constituent unit of a polysaccharide (e.g., three hydroxyl groups in the case of cellulose) need not be completely modified with a vinylic compound as described above, but a polysaccharide may be chemically modified with a vinylic compound to such an extent that the chemically modified polysaccharide can be dissolved in a good solvent such as methylene chloride and the like, by which the objective polymerization of the modified polysaccharide on the surface of a support can be attained.

Meanwhile, the porous support to be applied such a polysaccharide having vinyl groups introduced thereinto according to the present invention includes known ones such as inorganic porous supports, e.g., silica, alumina, magnesia, titanium oxide, glass, silicates, kaolin, etc., and organic porous supports, e.g., polystyrene, polyamide, polyacrylate, etc., among which porous particles such as silica (silica gel) and glass (porous glass) are preferably used.

In the present invention, these porous supports may be each used as such or may be modified by the introduction of vinyl groups prior to the use for supporting the polysaccharide having vinyl groups introduced thereinto more effectively. In the latter case, copolymerization between the polysaccharide having vinyl groups introduced thereinto and the porous support having vinyl groups introduced thereinto is conducted to thereby provide an optical resolution agent insolubilized in organic solvents, more effectively.

Various known processes can be employed in the introduction of vinyl groups into a porous support. The introduction can be conducted by the method same as one for bonding vinyl groups to a polysacchalide described above. Namely, a given porous support, preferably a chemically modifiable support such as silica gel, porous glass, etc., is reacted with a vinylic compound which may have more than one vinyl group or may have a vinyl group at any position to such an extent as to exert little adverse effect on the function of the copolymerizability to bond the vinylic compound to the porous support. Therefore, objective vinyl groups are introduced into the porous support.

Specific processes for introducing vinyl groups to a porous support will now be listed next, wherein silica gel is used as the porous support.

I. Process for reacting a silylating agent having a vinyl group with the hydroxyl group of silica gel

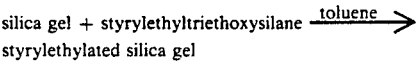
styrylethylated silica gel

II. Process for introducing a functional group reactive with a compound having a vinyl group to the surface of silica gel and bonding vinyl groups to the resulting surface (1) 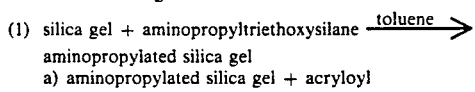
aminopropylated silica gel
a) aminopropylated silica gel + acryloyl
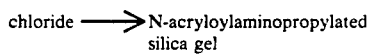
b) aminopropylated silica gel + methacryloyl
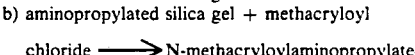
c) aminopropylated silica gel + vinylphenyl
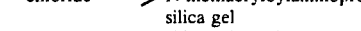
(2) silica gel + O-trimethylsilylpropyldimethylchloro-
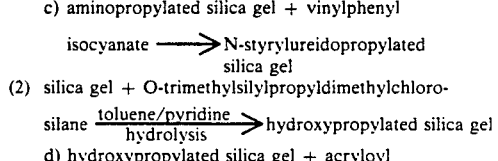
d) hydroxypropylated silica gel + acryloyl
chloride ⟶ N-acryloylhydroxypropylated silica gel
e) hydroxypropylated silica gel + vinylphenyl
isocyanate ⟶ N-styrylcarbamoyloxypropylated silica gel
(3) silica gel + glycidoxypropyltrimethoxy-
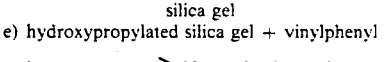
f) glyceroylpropylated silica gel + acryloyl
chloride ⟶ O-acryloylglyceroylpropylated silica gel III. Process for bonding a silylating agent with a compound having a vinyl group and then bonding the reaction product to silica gel
a) aminopropyltriethoxysilane + acryloyl
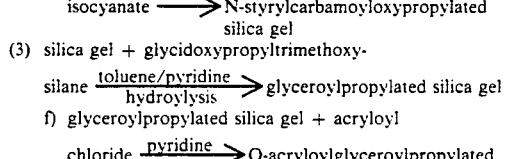
b) aminopropyltriethoxysilane + methacryloyl
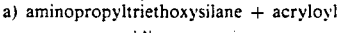
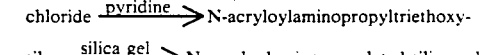
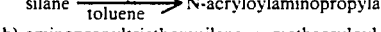
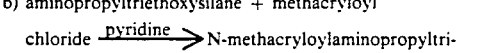
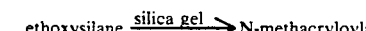
c) aminopropyltriethoxysilane + vinylphenyl
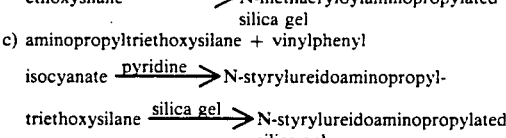

Since the above-described porous support is used in the present invention, the processes for the preparation of an optical resolution agent which is described above and which is prepared by polymerizing a polysaccharide having vinyl groups introduced thereinto are classified roughly into two groups, i.e., a group consisting of processes using a support having vinyl groups bonded thereto as the porous support and a group consisting of processes using a support having no vinyl group. A support having vinyl groups introduced thereinto and an unmodified support are different from each other in respect of surface polarity, so that they may be different from each other in the amount of adsorption of the vinylated polysaccharide and may release the polysaccharide during the polymerization to different extents in these preparation processes, especially when a polysaccharide having vinyl groups introduced thereinto is adsorbed to each of the supports. However, same procedure can be applied to both of the supports with respect to the adsorption process and polymerization conditions. For example, the optical resolution agent according to the present invention can be prepared by applying a solution of the polysaccharide having vinyl groups introduced thereinto to the surface of a support to cause the polysaccharide to be adhered or adsorbed on the surface and polymerizing the polysaccharide by a polymerization method such as radical, ionic or plasma polymerization.

When an unmodified porous support is used, the polysaccharide derivative may be eluted when the degree of polymerization of the polymer is low, though the object of preventing the dissolution of the polysaccharide derivative even in a good solvent such as methylene chloride can be attained by enhancing the degree of polymerization of the polysaccharide derivative to such an extent that the polymer cannot be dissolved in the good solvent. On the other hand, when a support having vinyl groups introduced thereinto is used, the polysaccharide derivative is bonded to the support, which prevents the elution of a polymer of the polysaccharide derivative, even if the polymer cannot acquire such a high degree of polymerization as to inhibit dissolution thereof even in a good solvent.

Further it is possible to employ a process for further causing the polysaccharide having vinyl groups bonded thereto to be adsorbed to the optical resolution agent prepared by the above polymerization to increase the amount of the polysaccharide derivative introduced and polymerizing the polysaccharide derivative to further enhance the degree of polymerization, because it is inconceivable that all of the vinyl groups present in both the polysaccharide derivative and the support are completely polymerized and disappear by only one run of polymerization. In such a process of conducting two or more runs of polymerization, a means, which comprises using a compound having more than one vinyl group, such as divinylbenzene, ethylenediamine dimethacrylate, ethylene glycol diacrylate and the like, as a crosslinking agent in addition to the polysaccharide derivative having vinyl groups bonded thereto to accelerate the crosslinking reaction and thereby the solubility of the polysaccharide derivative polymer in a good solvent being able to be further lowered, can also be employed.

As the polymerization condition for preparing the polymeric optical resolution agent according to the present invention, general conditions used for suspension polymerization can be applied. When water is used as the medium for the polymerization, however, the ester groups bonded to the polysaccharide may be hydrolyzed and the polysaccharide having vinyl groups introduced thereinto adsorbed on a porous support through a hydrogen bond may be released from the surface of the support owing to the cleavage of the hydrogen bond between the polysaccharide and the porous support caused by the intervention of water. The falling off of the functional groups including a vinyl group introduced the polysacharide brings about a lowering in the optical resolving power, and a lowering in the amount of adsorption of the vinylated polysaccharide on the porous surface in the polymerization step is thought to be causative of a lowering in the efficiency of introducing the polysaccharide derivative into the porous surface. For these reasons, it is desired for the polymerization of the polysaccharide derivative on the porous surface that a solvent which neither hydrolyzes the ester or urethane linkage nor lowers the amount of adsorption of the polysaccharide derivative is selected, compared with a process which comprises using water as the medium.

Although the polymerization medium which neither decomposes the ester or urethane linkage nor cleaves the hydrogen bond includes low-polarity organic solvents, the use of a solvent which has a boiling point of 90° C. or above and is liquid at ordinary temperatures is preferable in consideration of the fact that the polysaccharide derivative is soluble in relatively many solvents and the requirement that the reaction temperature necessary for radical polymerization must be secured. For these reasons, alkyl hydrocarbons are thought to be optimum as the medium to be used in the preparation of the optical resolution agent. As specific examples of the alkyl hydrocarbon mediums, a straight-chain hydrocarbon having 7 or more carbon atoms, such as heptane, optane, nonane, decane and the like; a molecular hydrocarbon having 7 or more carbon atoms, such as isooctane and the like; a cyclic hydrocarbon such as decalin and the like; and a hydrocarbon mixture such as kerosine and the like are advantageously used.

The polysaccharide derivative having vinyl groups introduced thereinto, which are adhered or adsorbed on the surface of a porous support, is polymerized to form a layer of a polymeric product of such a polysaccharide derivative on the surface of the support. Particularly, when a porous support having vinyl groups introduced thereinto is used, copolymerization also occurs between the support and the polysaccharide derivative, so that the polymerization product is insoluble in organic solvents at all. Thus, an optical resolution agent which is insolubilized against organic solvents can be obtained advantageously.

Actually, there has been ascertained that when the insobubilized optically active support of a polysaccharide polymerization type is used as a packing for high-performance liquid chromatography, optical resolution can be attained even under such mobile phase conditions that the polysaccharide derivative is dissolved to fail in optical resolution when the optical resolution agent of the prior art prepared only by causing a chemically modified polysaccharide to be adsorbed to silica gel as the base material is employed, and that the insolubilized optically active support of a polysaccharide polymerization type is to become a support of a polymerization type, the performance of which is not lowered and the optical resolving power of which is maintained as such even after the injection and passing of methylene chloride, which is a representative good solvent for the polysaccharide derivative before polymerization.

EXAMPLE

Figure 1:
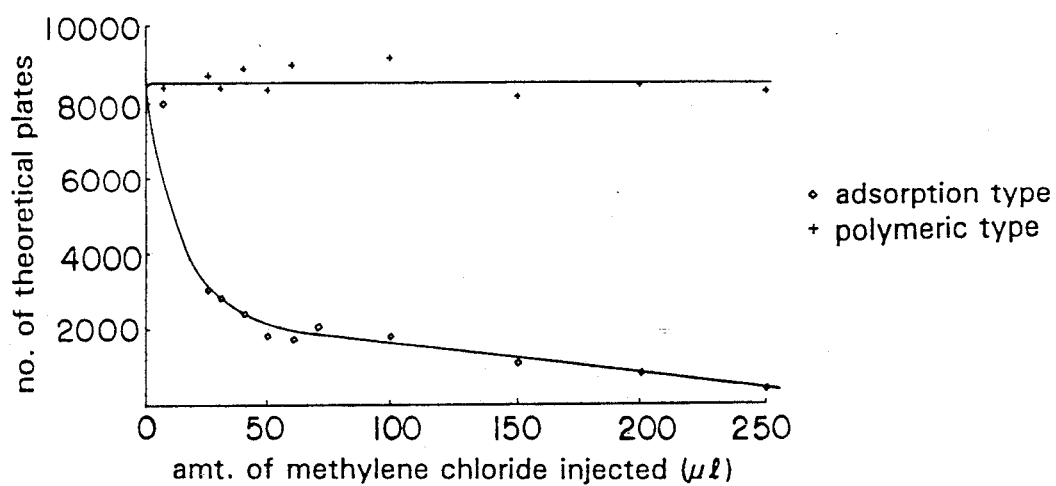
FIGS. 1 and 2 are graphs respectively showing changes in the number of theoretical plates and the relative retention value with an increase in the amount of methylene chloride injected, which were observed in Example 2.

Examples according to the present invention will now be given in order to illustrate the present invention more specifically, though it is needless to say that the present invention is not limited by the description of the Examples at all. Further, it should be noted that the embodiments described in the Examples and the specific descriptions mentioned above can be changed, modified or improved by those skilled in the art in such a range as not to deviate from the gist of the present invention.

EXAMPLE 1

16.8 g of a low-molecular weight cellulose (having a degree of polymerization of about 36) prepared by hydrolyzing acetylcellulose to reduce the molecular weight thereof and removing the acetyl groups therefrom was dispersed in 250 ml of pyridine, followed by the addition of 89.0 g of 4-vinylbenzoyl chloride. The obtained mixture was heated to 80° C. and reacted under stirring for 10 hours. After the completion of the reaction, the reaction mixture was poured into 1000 ml of methanol to precipitate 4-vinylbenzoylated cellulose, which was washed with methanol under filtering by the means of suction and dried at 50° C. The resulting product was dissolved in 500 ml of methylene chloride to filter out insolubles. The filtrate was distilled to remove the methylene chloride. Methanol was added to the residue to precipitate a solid. The FT-IR spectrum of the cellulose derivative had an absorption peak assignable to a carbonyl group, by which it was ascertained that the hydroxyl groups of the glucose, which was a constitution unit of the cellulose, were derived.

Then, 4 g of silica gel as a porous support was dispersed in a solution of 1 g of the 4-methylbenzoylated cellulose in 50 ml of methylene chloride. The obtained dispersion was distilled in a vacuum at 30° C. to remove the methylene chloride, thereby causing the cellulose derivate to be adhered or adsorbed on the surface of the silica gel.

Thereafter, 3 g of the silica gel having 4-vinylated cellulose adsorbed thereto was dispersed in 50 ml of n-heptane, followed by the addition of 30 mg of benzoyl peroxide. The obtained mixture was stirred at 80° C. for 4 hours to conduct polymerization, by which a layer of a polymeric product of 4-vinylbenzoylated cellulose was formed on the surface of the silica gel. After the completion of the polymerization reaction, the resulting silica gel having the layer of a polymeric product formed was washed with methylene chloride and dried in a vacuum.

The obtained silica gel having the layer of a polymeric product of 4-vinylbenzoylated cellulose formed was examined for solubility. As a result, it was ascertained that the silica gel of this Example was superior to one having acetylcellulose, low-molecular weight cellulose or 4-vinylbenzoylated cellulose adsorbed on the surface thereof in respect of the insolubility in organic solvents and that the optical resolving power could be fully retained even after the adsorbed cellulose derivative was polymerized.

EXAMPLE 2

An N-acryloylaminopropylated silica gel as a support having vinyl groups introduced thereinto was prepared as follows.

Namely, first, 2 g of vacuum-dried silica gel was dispersed in 100 ml of toluene, followed by the addition of 2 g of aminopropyltriethoxysilane as a silylating agent. The obtained mixture was reacted for 5 hours while distilling off the ethanol formed by the reaction of the silylating agent with the silanol together with the toluene. Thus, an aminopropylated silica gel was obtained. After the completion of the reaction, the aminopropylated silica gel was washed with methanol, 80% methanol, methanol and chloroform, successively, and dried in a vacuum.

Then, 2 g of the above aminopropylated silica gel was dispersed in 50 ml of chloroform, followed by the addition of 2 ml of acryloyl chloride. The obtained mixture was maintained at 80° C. for 2 hours to conduct a reaction, giving an N-acryloylaminopropyl silica gel. After the completion of the reaction, the product was washed with methanol and chloroform, successively, and vacuum dried.

The N-acryloylaminopropylated silica gel thus obtained was used. For causing the 4-vinylbenzoylated cellulose prepared in the Example 1 to be adsorbed on the surface of the silica gel, 1 g of the cellulose derivative was dissolved in 50 ml of methylene chloridethe to prepare a solution, the above-described N-acryloylaminopropylated silica gel was added to and dispersed in the solution, and the obtained mixture was distilled in a vacuum at 30° C. to remove the methylene chloride, thus causing the cellulose derivative to be adsorbed on the surface of the silica gel.

Further, then, 3 g of the N-acryloylaminopropyl silica gel wherein the 4-vinylbenzoylated cellulose was adsorbed thereto was dispersed in 50 ml of n-heptane, followed by the addition of 30 mg of benzoyl peroxide. The obtained mixture was stirred at 80° C. for 4 hours to copolymerize the acryloyl groups (vinyl groups) introduced into the silica gel with the 4-vinylbenzoylated cellulose, thus giving a polymeric optical resolution agent wherein the cellulose derivative was chemically bonded to the surface of the silica gel.

The polymeric optical resolution agent thus prepared was used as a packing which was packed in a column of a high-performance liquid chromatography apparatus to determine the influences of the injection of methylene chloride on the number of theoretical plates and the retention as compared with the case that an optical resolution agent comprising a silica gel wherein 4-vinylbenzoylated cellulose was only adsorbed on the surface of the silica gel was used as an adsorption-type packing. That is, both the adsorption-type and polymeric cellulose derivative packings were examined for the influences of the injection of methylene chloride on the number of theoretical plates with respect to benzene and the retention time of stilbene oxide. The results are given in FIGS. 1 and 2.

Figure 2:
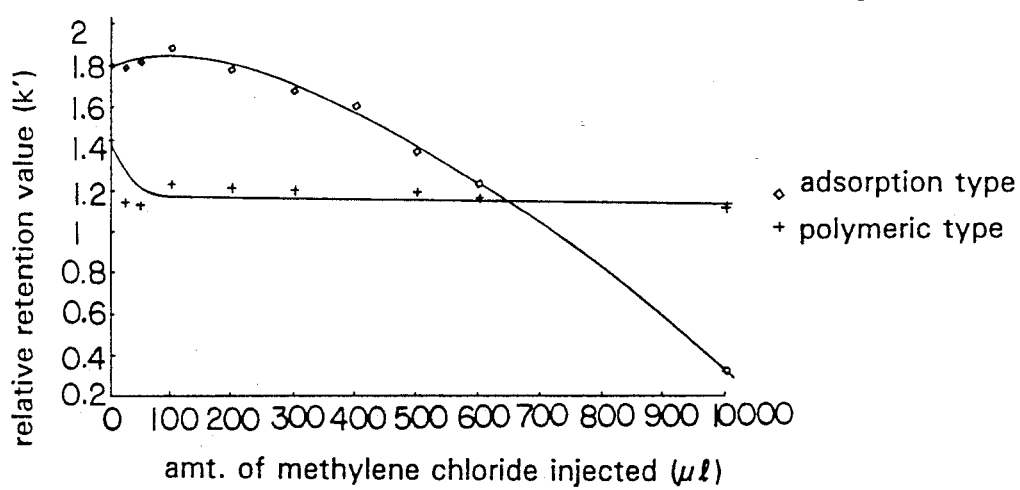

As shown in FIGS. 1 and 2, the number of theoretical plates of the adsorption-type packing lowered to 3000 from the initial value of about 8300 by the injection of 20 μl of methylene chloride, and to below 1000 by the injection of 200 μl thereof, which can be presumed that the number of theoretical plates was lowered because the methylene chloride injected might dissolve part of the cellulose derivative to disturb the stationary phase.

Further, the retention time was not affected by the injection of about 20 to 50 μl of methylene chloride, therefore it was thought that the elution of the cellulose derivative was not occured. When 100 μl or above of methylene chloride was injected at once, however, the retention rapidly lowered and the elution of the cellulose derivative was observed. From these results, it can be understood that methylene chloride cannot be used as a solvent for dissolving a sample when the adsorption-type packing is used and it can be presumed that such a lowering in the retention will occur similarly when a solvent having a solubility parameter of about 18 to 25 is injected.

On the other hand, when the polymeric, chemically bonded packing of the present invention was used, no difference was observed in retention time, the number of theoretical plates or optical resolving power before and after the injection of methylene chloride, which clearly showed that the packing of the present invention is extremely excellent in the insolubility in organic solvents.

Figure 3B:
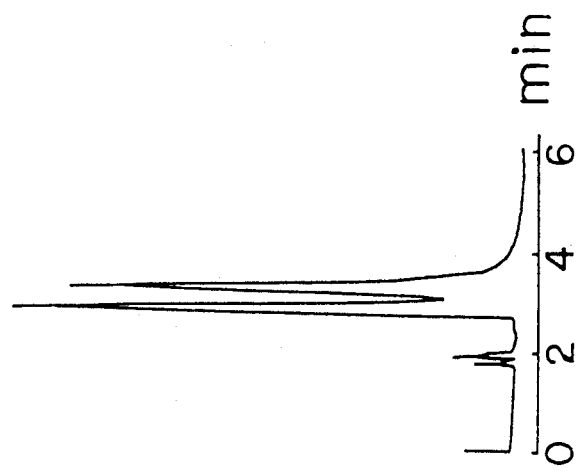
FIGS. 3(a) and (b) are chromatograms observed in Example 2 with different the compositions of the mobile phases each other.
Figure 3A:
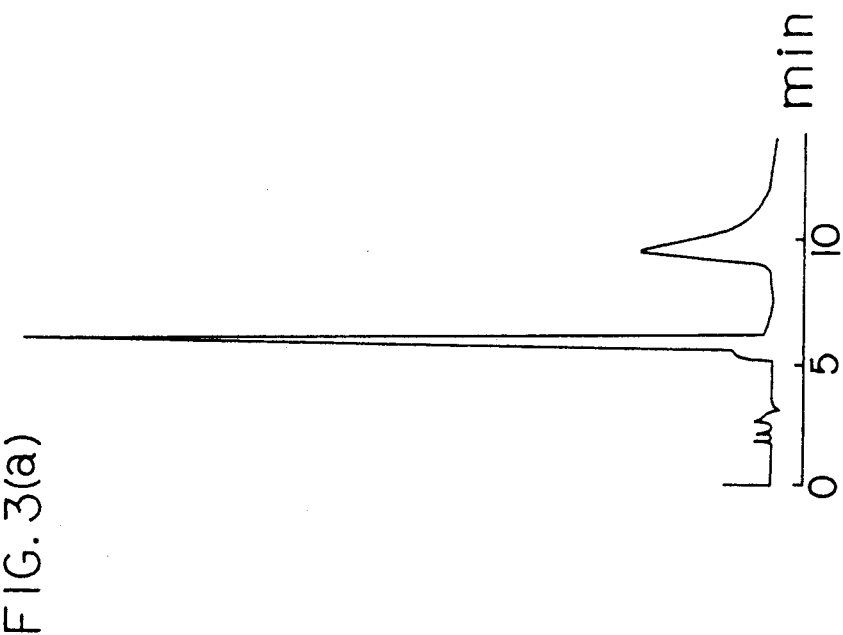

Further, the optical resolving powers exhibited were examined in the case of using a mobile phase containing tetrahydrofuran, which is a good solvent for the cellulose derivative, as an additive. As a result, as shown in FIGS. 3(a) and (b), it was ascertained that the polymeric packing according to the present invention exhibited an optical resolving power even when a mobile phase containing 30% of tetrahydrofuran (THF) was used and that the optical resolving power was maintained even when 50% of tetrahydrofuran was contained in the mobile phase. The gas chromatography was conducted under the following conditions:

column: polymeric vinylbenzoylcellulose
column sizes: 4.6 mm (inner diameter)×150 mm (length)
mobile phase:
  (a) hexane/THF (7:3)
  (b) hexane/THF (5:5)
flow rate: 1.0 ml/min
detection: UV (254 nm)
sample: warfarin.

On the other hand, in the case of using the adsorption-type packing wherein 4-vinylbenzoylated cellulose was only adsorbed, the elution of the stationary phase was observed when only 30% of tetrahydrofuran was added, and the chromatographic analysis was impossible because of a lowered retention and a disturbed base line.

As described above, the optical resolution agent according to the present invention prepared by polymerizing a polysaccharide derivative on the surface of a porous support exhibits an optical resolving power equivalent to that of the adsorption-type optical resolution agent of the prior art prepared by causing a polysaccharide derivative to be adsorbed on the surface of a porous support. Further, the polysaccharide derivative is not eluted even with an organic solvent which could not be used for the adsorption-type optical resolution agents when the optical resolution agent according to the present invention is employed. Thus, the optical resolution agent according to the present invention is extremely useful as a polysaccharide derivative type one which permits the use of various organic solvents.

We claim:

1. An optical resolution agent prepared by polymerizing a polysaccharide derivative having vinyl groups introduced into the hydroxyl groups thereof through an ester or urethane linkage on the surface of a porous support.

2. An optical resolution agent prepared by copolymerizing a polysaccharide derivative having vinyl groups introduced into the hydroxyl groups thereof through an ester or urethane linkage with a porous support having vinyl groups introduced thereinto.

3. A process for the preparation of an optical resolution agent, characterized by causing a polysaccharide derivative having vinyl groups introduced into the hydroxyl groups thereof through an ester or urethane linkage to be adhered or adsorbed on the surface of a porous support and polymerizing the polysaccharide derivative.

4. A process for the preparation of an optical resolution agent, characterized by causing a polysaccharide derivative having vinyl groups introduced into the hydroxyl groups thereof through an ester or urethane linkage to be adhered or adsorbed on the surface of a porous support having vinyl groups introduced thereinto and polymerizing the polysaccharide derivative with at least part of the polysaccharide derivative being copolymerized with the vinyl groups of the porous support.

5. A process for the optical resolution of a racemic modification with the optical resolution agent as set forth in claim 1.

6. A process for the optical resolution of a racemic modification with the optical resolution agent as set forth in claim 2.

* * * * *